(12) United States Patent
Hu et al.

(10) Patent No.: US 11,402,620 B2
(45) Date of Patent: Aug. 2, 2022

(54) AMPLIFIABLE NANOPARTICLE ENHANCED QUANTITATIVE SCATTERING ASSAY UNDER LOW MAGNIFICATION DARK FIELD MICROSCOPE

(71) Applicant: ARIZONA BOARD OF REGENTS ON BEHALF OF ARIZONA STATE UNIVERSITY, Scottsdale, AZ (US)

(72) Inventors: Ye Hu, New Orleans, LA (US); Dali Sun, West Fargo, ND (US); Christopher Lyon, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/420,102

(22) PCT Filed: Dec. 31, 2019

(86) PCT No.: PCT/US2019/069095
§ 371 (c)(1),
(2) Date: Jun. 30, 2021

(87) PCT Pub. No.: WO2020/142509
PCT Pub. Date: Jul. 9, 2020

(65) Prior Publication Data
US 2022/0043250 A1 Feb. 10, 2022

Related U.S. Application Data

(60) Provisional application No. 62/787,003, filed on Dec. 31, 2018.

(51) Int. Cl.
| | |
|---|---|
| G02B 21/26 | (2006.01) |
| G01N 1/31 | (2006.01) |
| G01N 1/44 | (2006.01) |
| G01N 1/38 | (2006.01) |
| G02B 21/00 | (2006.01) |
| G01K 7/02 | (2021.01) |
| G01N 33/483 | (2006.01) |
| G02B 21/36 | (2006.01) |
| G02B 21/10 | (2006.01) |

(52) U.S. Cl.
CPC .............. *G02B 21/26* (2013.01); *G01K 7/02* (2013.01); *G01N 1/312* (2013.01); *G01N 1/44* (2013.01); *G01N 33/483* (2013.01); *G02B 21/365* (2013.01); *G01N 2001/386* (2013.01); *G02B 21/0088* (2013.01); *G02B 21/10* (2013.01)

(58) Field of Classification Search
CPC ........ G01N 1/44; G01N 1/312; G01N 33/483; G02B 21/10; G02B 21/0088; G02B 21/365
See application file for complete search history.

(56) References Cited

U.S. PATENT DOCUMENTS

| | | | |
|---|---|---|---|
| 8,298,793 B2 | 10/2012 | Vodyanoy et al. | |
| 9,513,224 B2 | 12/2016 | Mohan et al. | |
| 2014/0335511 A1* | 11/2014 | Glaser | G01N 1/286 435/6.1 |
| 2017/0022553 A1* | 1/2017 | Vijayan | C12Q 1/6869 |

FOREIGN PATENT DOCUMENTS

EP 2296367 B1 8/2016

OTHER PUBLICATIONS

Arruebo, M., et al. Antibody-conjugated nanoparticles for biomedical applications. J. Nanomater. 2009, (2009).
Bobrie, A., et al. Exosome Secretion: Molecular Mechanisms and Roles in Immune Responses. Traffic 12, 1659-1668 (2011).
Brisard, S. Overview of FFT-based homogenization techniques from the Galerkin point of view To cite this version?: Overview of FFT-based homogenization techniques from the Galerkin point of view. Conf. Int. Geotech. des Ouvrages Struct. 0-10 (2015).
Brown, S. D. et al. Gold Nanoparticles for the Improved Anticancer Drug Delivery of the Active Component of Oxaliplatin. J. Am. Chem. Soc. 132, 4678-4684 (2010).
Chen, R. et al. Ultrasound-Accelerated Immunoassay, as Exemplified by Enzyme Immunoassay of Choriogonadotropin. 30, 1446-1451 (1984).
Choi, C. H. J., et al. Mechanism of active targeting in solid tumors with transferrin-containing gold nanoparticles. Proc. Natl. Acad. Sci. 107, 1235-1240 (2010).
Chu, W. et al. Ultrasound-accelerated formalin fixation of tissue improves morphology, antigen and mRNA preservation. Mod. Pathol. 18, 850-863 (2005).
Cravotto, G. et al. Power ultrasound in organic synthesis?: moving cavitational chemistry from academia to innovative and large-scale applications. 180-196 (2006). doi:10.1039/b503848k.
Dreaden, E. C., et al. The golden age: gold nanoparticles for biomedicine. Chem. Soc. Rev. 41, 2740-2779 (2012).
Duijvesz, D., et al. Exosomes as biomarker treasure chests for prostate cancer. Eur. Urol. 59, 823-831 (2011).
Engvall, E. et al. Enzyme-Linked Immunosorbent Assay , Elisa?: III. Quantitation of Specific Antibodies by Anti-Immunoglobulin in Antigen-Coated Tubes Article cited in?: Information about subscribing to The Journal of article . Sign up at. J. Immunol. 109, 129-135 (1972).

(Continued)

*Primary Examiner* — Christopher Adam Hixson
(74) *Attorney, Agent, or Firm* — Quarles & Brady, LLP (57) ABSTRACT

The present disclosure relates a low magnification dark-field microscope system and method for producing a dark-field image. The method includes transferring a biological specimen to a surface of a sample plate, and pre-treating the biological specimen using one or more pre-treatment steps selected from (1) heating the biological specimen using a heating device; (2) applying ultrasound energy using an ultrasound transducer and ultrasound generator; and (3) doping the biological specimen with a metallic nanoparticle. Following pre-treatment, the method includes imaging a region of interest the biological specimen on the sample plate using a dark-field microscope to generate a dark-field image of the biological specimen.

20 Claims, 7 Drawing Sheets

(56) References Cited

OTHER PUBLICATIONS

Eustis, S. et al. Why gold nanoparticles are more precious than pretty gold: Noble metal surface plasmon resonance and its enhancement of the radiative and nonradiative properties of nanocrystals of different shapes. Chem. Soc. Rev. 35, 209-217 (2006).
Février, B. et al. Exosomes: Endosomal-derived vesicles shipping extracellular messages. Curr. Opin. Cell Biol. 16, 415-421 (2004).
Ghosh, S. K. et al. Interparticle Coupling Effect on the Surface Plasmon Resonance of Gold Nanoparticles: From Theory to Applications. Chem. Rev. 107, 4797-4862 (2007).
Green, D. J., et al. Adaptive Focused Acoustics (AFA) Improves the Performance of Microtiter Plate ELISAs. J. Biomol. Screen. 19, 1124-30 (2014).
Haiss, W., et al. Determination of size and concentration of gold nanoparticles from UV-Vis spectra. Anal. Chem. 79, 4215-4221 (2007).
Hawkes, J. J., et al. Ultrasonic deposition of cells on a surface. Biosens. Bioelectron. 19, 1021-1028 (2004).
Im, H. et al. Label-free detection and molecular profiling of exosomes with a nano-plasmonic sensor. Nat. Biotechnol. 32, 490-5 (2014).
International Searching Authority. International Search Report and Written Opinion for application PCT/US2019/069095, dated Mar. 17, 2020.
Jain, P.K., et al. "Calculated absorption and scattering properties of gold nanoparticles of different size, shape, and composition: applications in biological imaging and biomedicine." The journal of physical chemistry B 110.14 (2006): 7238-7248.
Jain, S., et al. Gold nanoparticles as novel agents for cancer therapy. Br. J. Radiol. 85, 101-113 (2012).
Johnson, K. A. et al. The original Michaelis constant: Translation of the 1913 Michaelis-Menten Paper. Biochemistry 50, 8264-8269 (2011).
Keller, S., et al. Exosomes: From biogenesis and secretion to biological function. Immunol. Lett. 107, 102-108 (2006).
Koshland, D. E., et al. Comparison of experimental binding data and theoretical models in proteins containing subunits. Biochemistry 5, 365-385 (1966).
Liang, K. et al. Nanoplasmonic quantification of tumour-derived extracellular vesicles in plasma microsamples for diagnosis and treatment monitoring. Nat. Biomed. Eng. 1, 0021 (2017).
López-Fidalgo, J. et al. Design Issues for the Michaelis-Menten Model. J. Theor. Biol. 215, 1-11 (2002).
Markovich, G., et al. "Architectonic quantum dot solids." Accounts of Chemical Research 32.5 (1999): 415-423.
McPherson, G. A. A practical computer based approach to the analysis of radioligand binding experiments. Comput Prog Biomed 17, 107-114 (1983).
Mullen, R., et al. Simulation of light scattering from Brownian particles. 1-17 (2015).
Niidome, T., et al. "PEG-modified gold nanorods with a stealth character for in vivo applications." Journal of Controlled Release 114.3 (2006): 343-347.
Parsons, J., et al. A comparison of techniques used to simulate the scattering of electromagnetic radiation by metallic nanostructures. Journal of Modern Optics 57, (2010).
Peinado, H. et al. "Melanoma exosomes educate bone marrow progenitor cells toward a pro-metastatic phenotype through MET." Nature medicine 18.6 (2012): 883-891.
Sendroiu, I. E., et al. "Plasmon interactions between gold nanoparticles in aqueous solution with controlled spatial separation." Physical Chemistry Chemical Physics 8.12 (2006): 1430-1436.
Simakova, P., et al. "Polyethylene-glycol-stabilized ag nanoparticles for surface-enhanced raman scattering spectroscopy: Ag surface accessibility studied using metalation of free-base porphyrins." The Journal of Physical Chemistry C 118.14 (2014): 7690-7697.
Somerville, W. R. C., et al. Smarties: User-friendly codes for fast and accurate calculations of light scattering by spheroids. J. Quant. Spectrosc. Radiat. Transf. 174, 39-55 (2016).
Sun, D. DarkScatterMaster. (2016). Available at: https://github.com/DaliSun/DarkScatterMaster_Macro.git. Accessed on Mar. 10, 2022.
Sun, D. et al. "Simulation-directed amplifiable nanoparticle enhanced quantitative scattering assay under low magnification dark field microscopy." Journal of Materials Chemistry B 8.25 (2020): 5416-5419.
Sun, D. et al. A low cost mobile phone dark-field microscope for nanoparticle-based quantitative studies. Biosens. Bioelectron. 99, 513-518 (2018).
Sun, D. et al. Noise Reduction Method for Quantifying Nanoparticle Light Scattering in Low Magnification Dark-Field Microscope Far-Field Images. Anal. Chem. 88, 12001-12005 (2016).
Sun, D., et al. A low-cost portable electrical sensor for hydroxyl ions based on amorphous InGaZnO4 thin film at room temperature. Sensors Actuators B. Chem. 239, 679-687 (2017).
Sun, D., et al. Hydroxyl radical and thermal annealing on amorphous InGaZnO4 films for DNA immobilizations. Colloids Surfaces B Biointerfaces 130, 119-125 (2015).
Sun, D., et al. Surface treatment on amorphous InGaZnO4 thin film for single-stranded DNA biosensing. Appl. Surf. Sci. 324, 310-318 (2015).
Talley, C. E. et al. Surface-enhanced Raman scattering from individual Au nanoparticles and nanoparticle dimer substrates. Nano Lett. 5, 1569-1574 (2005).
Terouanne, B., et al. "Bioluminescent immunosorbent for rapid immunoassays." Analytical biochemistry 154.1 (1986): 118-125.
Towbin, H., et al Electrophoretic transfer of proteins from polyacrylamide gels to nitrocellulose sheets: procedure and some applications. Proc. Natl. Acad. Sci. U. S. A. 76, 4350-4 (1979).
Van Dijk, M. et al. Absorption and scattering microscopy of single metal nanoparticles. Physical Chemistry . . . 1-33 (2006). doi:10.1039/b606090k.
Ventola, C. L. "Progress in nanomedicine: approved and investigational nanodrugs." Pharmacy and Therapeutics 42.12 (2017): 742.
Zhang, G., et al. "Influence of anchoring ligands and particle size on the colloidal stability and in vivo biodistribution of polyethylene glycol-coated gold nanoparticles in tumor-xenografted mice." Biomaterials 30.10 (2009): 1928-1936.
Zhu, L. et al. Label-free Quantitative Detection of Tumor-derived Exosomes through Surface Plasmon Resonance Imaging. Anal. Chem. (2014). doi:10.1021/ac5023056.

\* cited by examiner

AMPLIFIABLE NANOPARTICLE ENHANCED QUANTITATIVE SCATTERING ASSAY UNDER LOW MAGNIFICATION DARK FIELD MICROSCOPE

CROSS REFERENCE TO RELATED APPLICATIONS

This application is a national stage filing under 35 U.S.C. § 371 of International Application No. PCT/US2019/069095, filed Dec. 31, 2019, which claims priority to U.S. Provisional Patent Application No. 62/787,003, filed on Dec. 31, 2018, which is incorporated by reference herein in its entirety.

BACKGROUND

The nanoscale of nanomaterials offers comparable sizes to biological molecules improving the interactions between them, thus holds great potential for health issues and biological research. Gold nanoparticles are fully developed as therapeutic and diagnostic agents both in vitro and in vivo due to their physicochemical properties. Substantial effort has been addressed in terms of developing gold nanoparticle-based biosensors for noninvasive and targeted tumor diagnosis and treatment. However, translational clinical applications are rare, and suffer from a trade-off between sensitivity and usability.

Dark-field microscope based nanoparticle quantitative assay suffers similarly. For example, dark-field microscope based nanoparticle quantitative assay suffers from operation complexity as it inevitably involves intensive manual focus adjustment and positioning which require an experienced operator and is time-consuming. Additionally, a limited view area under high magnification makes it hard to observe all regions of interest (ROI), and normally several views within the ROI are manually selected for averaging, which introduces artificial bias. Utilizing low power objective lenses are also problematic regarding quantification in low magnification dark-field assay. For example, large view area induces condemnations, dents, and scratches which disturb the resultant image and lower the signal-to-noise ratio (SNR).

Currently, there is a need for improvements to existing dark-field microscope based nanoparticle quantitative assay systems and, in particular, there is a need to develop new techniques to improve sensitivity and reduce inhomogeneity bias.

SUMMARY OF THE DISCLOSURE

The present disclosure addresses the aforementioned drawbacks of conventional low magnification dark-field assay (LMDFA) systems and methods. In some embodiments, the present disclosure includes one or more pre-treatment steps, such as heating, ultrasound and/or a signal amplification scheme to improve homogenous distribution and sensitivity of the biological specimen on the sample plate during imaging.

Some embodiments provide a process for using a low magnification dark-field microscope system to produce a dark-field image of a biological specimen. In particular, the process includes transferring a biological specimen to a surface of a sample plate, and heating the biological specimen using a heating device in an amount sufficient to enhance the binding affinity of the biological specimen to the sample plate. Additionally or alternatively, ultrasound energy is applied to the biological specimen in an amount sufficient to enhance the binding affinity of the biological specimen to the sample plate. The ultrasound energy is applied using an ultrasound transducer communicatively coupled to an ultrasound generator. The method further includes imaging a region of interest of the biological specimen on the sample plate using a dark-field microscope to generate a dark-field image of the biological specimen.

Some embodiments of the disclosure further include processing the dark-field image of the biological specimen to determine an amount of the biological specimen within the region of interest.

In further embodiments, transferring the biological specimen to the surface of the sample plate further includes doping the biological specimen with one or more metallic nanoparticle to improve signal amplification during generation of the dark-field image. In particular, the one or more metallic nanoparticle dopant comprises a first protein modified with a first metallic nanorod, a second protein modified with a second metallic nanorod; and a linker that couples the first protein to the second protein. The first and second protein may comprise streptavidin, and the first and second metallic nanorod may comprise gold nanorods. The linker may comprise bis-biotin coupled through functionalized polyethylene glycol.

These and other advantages and features of the present invention will become more apparent from the following detailed description of the preferred embodiments of the present invention when viewed in conjunction with the accompanying drawings.

DESCRIPTION OF THE DRAWINGS

The present embodiments of this disclosure will be better understood and features, aspects and advantages other than those set forth above will become apparent when consideration is given to the following detailed description thereof. Such detailed description makes reference to the following drawings, wherein:

FIGS. 5($a$-$h$) illustrate various treatment effects including: a) a schematic chart of the direct binding assay; b) The response and sum of square variance change by ultrasound treatment. c) schematic chart of the sandwich binding assay; d, e) the response change by ultrasound and heat respectively; f) schematic chart of the nanoparticle quantification assay; g, h) the linearity and within-run CV of response towards particle concentration comparing with non-treated assay.

FIGS. 6($a$-$b$) illustrate the effect of treatment towards exosome immobilization including: a) AFM images of exosomes without the treatment and b) with the treatment. The particle size distribution charts at the bottom are from particle analysis of AFM. The insets on the left corner are SEM images of the exosomes.

FIGS. 7($a$-$f$) are modeling data and simulations including: a) a simulation scheme for signal amplification; b) scatter intensity verse distance of the particles at 650 nm; c) wavelength scan verse distance of the particles; d) sum of scatter intensity of all wavelength verse distance of the particles; e) simulation scheme for nanoparticle cluster; f) scatter intensity verse number of the particles.

FIGS. 8(a-g) provide signal amplification schemes and imaging data including: a) signal amplification scheme; b) UV-IR absorption spectrum of unlinked and linked particle solution; c, d) UV-IR absorption spectrum and intensity at 650 nm towards linker concentration; e) SEM images of unlinked and linked AuNR; f, g) Amplified LMDFA scheme and response comparison.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the disclosure. Various modifications to the illustrated embodiments will be readily apparent to those skilled in the art, and the generic principles herein can be applied to other embodiments and applications without departing from embodiments of the disclosure. Thus, embodiments of the disclosure are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the disclosure. Skilled artisans will recognize the examples provided herein have many useful alternatives and fall within the scope of embodiments of the disclosure.

The present disclosure addresses the aforementioned drawbacks of conventional low magnification dark-field assay (LMDFA) systems and methods. In some embodiments, the present disclosure includes one or more pre-treatment steps and/or a signal amplification scheme to improve homogenous distribution of the biological specimen and sensitivity during imaging.

Figure 1:
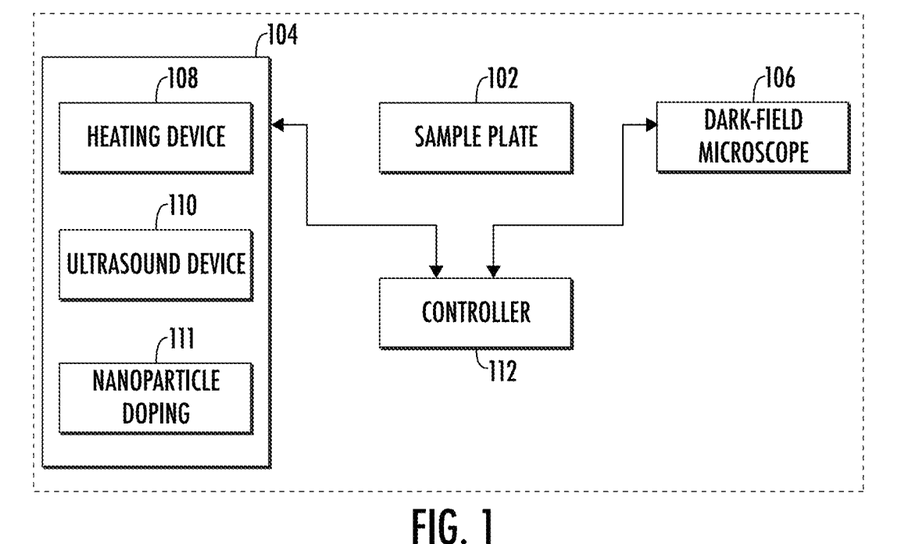
FIG. 1 is a block diagram of a dark-field microscope system in accordance with the present disclosure.

Dark-Field Microscope System:

Referring to FIG. 1, an example block diagram of a dark-field microscope system 100 is illustrated that can produce a dark-field image in accordance with embodiments of the present disclosure. Generally, the dark-field microscope system 100 includes a sample plate 102 having a surface configured to receive a biological specimen (e.g., protein, antibody, nanoparticle, exosome, cell, etc.), a pre-treatment station 104 configured with one or more pre-treatment devices or steps for treating the biological specimen, and a dark-field microscope 106 configured to produce a dark field image of a region of interest of the biological specimen.

In some aspects, the pre-treatment station 104 includes a heating device 108 that is configured to transfer heat from a heat source to the biological specimen and sample plate 102. Additionally or alternatively, the pre-treatment station 104 may include an ultrasound device 110 configured to apply ultrasound energy to the biological specimen and sample plate 102. Heat and ultrasound energy may be applied by the heating device 104 and ultrasound device 110, respectively, in an amount sufficient to enhance the binding affinity and homogenous distribution of the biological specimen on the sample plate 102.

In some embodiments, the dark-field microscope system 100 includes one or more controller 112 that is communicatively coupled to the dark-field microscope 108, the heating device 108, and/or the ultrasound device 110. The controller 112 includes one or more processor, a memory and software stored therein for controlling the heating device 108, the ultrasound device 110, and the dark-field microscope 106 to perform and implement the processing tasks and methods described herein.

In some embodiments, the sample plate 102 may include a binding medium coupled to a surface on the sample plate 102 that is used to facilitate adhering the biological specimen to the surface of the sample plate 102. For example, the binding medium may be bound to a plurality of sample loading spots dispersed throughout the surface of the sample plate 102, or bound to the entire surface of the sample plate 102. Suitable binding mediums for use in the present disclosure include those that facilitate adhering the biological specimen to the surface of the sample plate 102, for example, through a covalent bond, ionic bond, hydrogen bond, polar bond, and combinations thereof.

Figure 2:
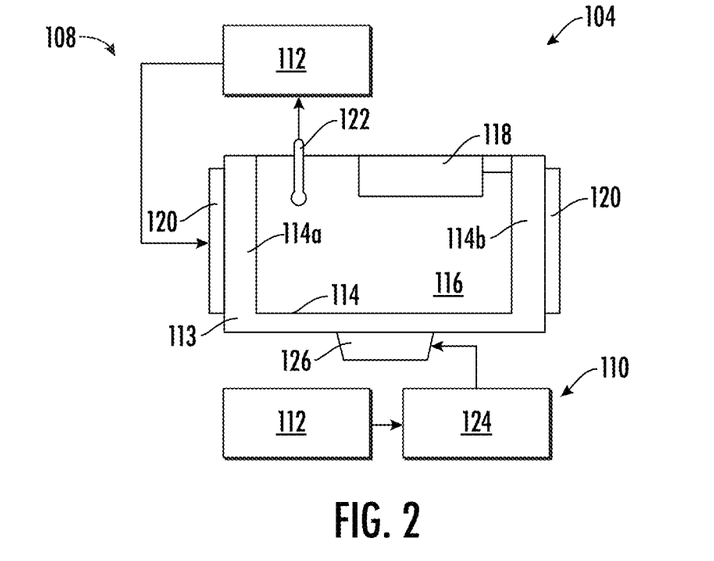
FIG. 2 is a schematic illustration of a pre-treatment device in accordance with the present disclosure.

FIG. 2 depicts an exemplary arrangement for a pre-treatment station 104. The pre-treatment station 104 includes a heating device 108 and an ultrasound device 110. In some embodiments, the pre-treatment station 104 includes a housing 113 having a bottom surface 114 and one or more side walls that longitudinally project therefrom (e.g., 114a and 114b). The housing 113 may be configured to receive a fluid medium 116 (e.g., water) that facilitates transferring heat from the heating device 108 to the biological specimen and sample plate 102. In some embodiments, the pre-treatment station 104 includes a sample holder 118 that is configured to receive the sample plate 102. The sample holder 118 may be coupled to the housing 113 such that at least a portion of the sample holder 118 is submerged within the fluid medium 116 to facilitate heat transfer to the sample plate 102 and biological specimen. As used herein, the term "portion" is used in its ordinary sense, refers, without limitation, to at least a part of a whole, and encompasses an amount, section, or piece of a thing (e.g., an amount or section of sample holder 118).

In some embodiments, the heating device 108 includes one or more heat source 120 configured to transfer heat to the fluid medium 116. The heat source 120 may be coupled to an outer surface of the housing 113 as illustrated in FIG. 2 or directly coupled to one or more of: the sample holder 118 and/or the sample plate 102. A non-limiting example of a heat source 120 suitable for use in the pre-treatment station 104 includes, but is not limited to, a heating tape communicative coupled to the controller 112 (e.g., Mega 2560 controller board with 2 channel 128V relay switch).

A temperature sensor 122, such as a thermocouple, may be used to monitor the temperature of the fluid medium 116 in the housing 113. In some embodiments, a controller 112 is communicatively coupled to the heat source 120 and the temperature sensor 122. The controller 112 may be programmed to adjust the temperature of the fluid medium 116 based on measured values obtained from the temperature sensor 122. For example, the controller 112 may adjust the temperature of the fluid medium 116 to maintain a desired set-point temperature or perform a pre-programmed temperature ramp function (e.g., increase or decrease the temperature of the fluid medium 116 over the duration of the pre-treatment step).

In some non-limiting examples, the controller 112 may regulate the temperature of the fluid medium 116 to maintain a temperature between 25 degrees Celsius to 75 degrees Celsius, or maintain a temperature between 30 degrees Celsius to 45 degrees Celsius. In some embodiments, the controller 112 is programmed to heat the biological specimen for a pre-selected duration, for example, for 30 seconds, or 1 minute, or 2 minutes, or 3 minutes, or 4 minutes, or 5 minutes, or 10 minutes, or 15 minutes, or 30 minutes, or 1 hour, or 1 day, and times therebetween.

Referring back to FIG. 2, the pre-treatment station 104 further includes an ultrasound device 110 that includes an ultrasound generator 124 configured to generate ultrasound energy and an ultrasound transducer 126 configured to direct the ultrasound energy at the biological specimen and sample plate 102. In some embodiments, the ultrasound transducer 126 is coupled to an outer surface of the housing 113. The ultrasound device 110 may include a controller 112 communicatively coupled to the ultrasound generator 124 and the ultrasound transducer 126. The controller 112 includes programming stored therein to adjust the amount of ultrasound energy applied and/or regulate the duration that ultrasound energy is applied to the biological specimen and sample plate 102. The controller 112 may control or regulate the ultrasound transducer 126 to emit ultrasound energy either continuously or intermittently. In some non-limiting examples, the controller 112 may regulate the ultrasound transducer 126 to apply ultrasound energy for a duration of 30 seconds, or 1 minute, or 2 minutes, or 3 minutes, or 4 minutes, or 5 minutes, or 10 minutes, or 15 minutes, or 30 minutes, or 1 hour, or 1 day, and times therebetween. In other non-limiting examples, the controller 112 may regulate the ultrasound transducer 126 to implement a user-specified pause between each respective pulse of ultrasound energy, such as a pause of 1 second, or 5 seconds, or 10 seconds, or 20 seconds, or 30 seconds, or more throughout the duration of applying ultrasound energy.

Referring back to FIG. 1, the pre-treatment station 104 may optionally further include doping the biological specimen on the sample plate 102 with one or more metallic nanoparticle to enhance the signal during dark-field imaging. In one non-limiting example, the one or more metallic nanoparticle includes a first protein modified with a first metallic nanorod, a second protein modified with a second metallic nanorod, and a linker that couples the first protein to the second protein. In one non-limiting example, the first and second protein comprise streptavidin modified with gold nanorods, and the linker comprises bis-biotin functionalized polyethylene glycol.

Following pre-treatment, the sample plate 102 may be transferred to the dark-field microscope 106 for imaging. The dark field microscope 106 may include an inverted microscope (e.g., TiS Eclipse; Nikon) equipped with an objective lens (e.g., 10× magnification, 4× magnification, or less) and a dark-field condenser (e.g., 1.2<NA<1.43). The sample plate 102 may be received on a motorized platform movable in X-Y-Z directions. A light source, such as a white light from a 100 W halogen lamp, may be used to shine light on the biological specimen. Scattered light may be acquired with a digital camera, such as a DS-Ri2 by Nikon, to generate data for dark-field color images.

In some embodiments, all sample spots on the sample plate 102 may be imaged using the motorized stage and an image stitching function that may be stored in the controller 112. Suitable image stitching functions may include, for example, NIS-Elements by Nikon. Image processing and quantification of the amount of biological specimen within the region of interest may be performed using a DarkScatterMaster (DSM) algorithm. In one non-limiting example, the DSM algorithm may be configured with the following software input parameters, which may be stored in the controller 112: contour threshold (Ct)=253.020, center scale (S)=0.8, type=Red, Low (Lt)/High (Ht) quantification limit: 0/62. In another non-limiting example, Limits of detection (LOD) and quantification (LOQ) were defined as 3× and 10× the standard deviation of the assay blank, respectively. Intra- and inter-assays coefficients of variation (CVs) were assessed from six replicates of the indicated samples. Graphs were generated with GraphPad Prism, Origin Pro 2017 and Microsoft Excel.

EXAMPLES

The following examples set forth, in detail, ways in which the dark-field microscope system 100 may be used to generate a dark-field image of the biological specimen and quantitatively identify the amount of biological specimen within a region of interest in the dark-field image. The following examples will enable one of skill in the art to more readily understand the principles thereof. The following examples are presented by way of illustration and are not meant to be limiting in any way.

Antibody Modification of Gold Nanorods (AuNRs).

Streptavidin functionalized nanorods AuNR-AV were purchased from Nanopartz (CZ12-25-650-NEUT-50, 5.1×$10^{12}$/mL). The coupling of antibodies and AuNRs followed the procedure: 40 μL AuNR were mixed with 20 μL PBS buffer and 20 μL biotinylated antibody solution (0.5 mg/ml) and shaken at room temperature for 3 hours (h) to complete the coupling process. The mixed solution was then washed 3 times: centrifuge at 6000 rpm for 10 minutes (min); remove the supernatant; solve the sediment with 200 μL PBS buffer. Finally, the antibody coupled AuNRs were re-suspended in 200 μL PBS buffer and stored at 4° C. before use.

Assay Process

Protein A/G and amine group functionalized glass slide patterned by proprietary hydrophobic mask was purchased from Arrayit Inc. (Sunnyvale, USA) with 192 sample loading spots. Protein A/G was immobilized as the target protein with a constant density of 1.1×$10^{10}$ proteins/mm$^2$, which was excessive. The surface is designed to bind human immunoglobulin proteins IgG1, IgG2, IgG3, IgG4 and all types of total IgG. Immobilization of the surface antibody was conducted by loading 1 μL antibody solution (0.05 mg/mL) per spot and incubated overnight at 4° C. Protein-Free Pierce blocking buffer (Thermo Scientific, USA) was added 1 μL per spot to block the surface free sites for 1 h at room temperature. The target solution sample (serum or antibody) was then loaded 1 μL per spot and incubated overnight at 4° C. Finally, antibody coupled nanoparticles were loaded to mark the targets for 2 h at room temperature.

For each solution addition onto the slides, a cleaning process was performed: vacuum out the leftover of the previous solution; wash the spot by loading 1 µL PBS to each spot; aspirate the PBS. The slide was then rinsed in with 0.01% Tween-20 in PBS (PBST, pH 7.0) for 10 min and then in DI water for 10 min. Before observation under DFM, the slides were air dried. Unless otherwise specified, all samples were repeated 6 times.

Exosomes Quantification Assay

Protein A/G functionalized glass slide patterned by proprietary hydrophobic mask was purchased from Arrayit Inc. (Sunnyvale, USA) with 192 sample loading spots. Protein A/G was immobilized as the target protein with a constant density of $1.1 \times 10^{10}$ proteins/mm$^2$, which was excessive. The surface is designed to bind human immunoglobulin proteins IgG1, IgG2, IgG3, IgG4 and all types of total IgG. Immobilization of the surface antibody was conducted by loading 1 µL antibody solution (0.05 mg/mL) per spot and accelerated as aforementioned. Superblock Pierce blocking buffer (Thermo Scientific, USA) was added 1 µL per spot to block the surface free sites for 1 h at room temperature. The target exosome solution sample was then loaded 1 µL per spot and incubated overnight at 4° C. Antibody coupled nanoparticles were then loaded to mark the targets for 2 h at room temperature after the aspiration of samples. For signal amplification, 1 µL per spot 5 mg/mL biotin functionalized polyethylene glycol (biotin-PEG-biotin, Mw: 400 and 1000 g/mol) were loaded on to the slides and incubated 1 h at room temperature. 40× diluted AuNR-AV were then loaded 1 uL to each spot for incubation of 1 h before rinsing of the slide. For each solution addition onto the slides, a cleaning process was performed: vacuum out the leftover of the previous solution; wash the spot by loading 1 µL PBS to each spot; aspirate the PBS. The slide was then rinsed in with 0.01% Tween-20 in PBS (PBST, pH 7.0) for 10 min and then in DI water for 10 min. Before observation under DFM, the slides were air dried. Unless otherwise specified, all samples were repeated 6 times.

AFM and SEM Imaging

AFM imaging was performed with a MultiMode AFM Nanoscope IV system (Bruker Instruments, Santa Barbara, Calif., USA) in tapping mode under ambient conditions. The images were recorded at a scanning rate of 1.5 Hz using an RTESPA-300 probe (Bruker Nano Inc., CA, USA) with a resonance frequency of ~320 kHz and a spring constant of ~40 N/m. Morphological studies were performed using scanning electron microscopy (FEI Nova NanoSEM 230) operated at 20 keV.

Simulation

The nanorods target used for calculations had a diameter of 25 nm and 60 nm in height (aspect ratio ~2.5). FDTD simulations confirming the enhancement of proximity particles by calculating scattering cross sections were performed by Lumerical FDTD Solutions. Mie approximation was conducted by SMARTIES, a T-Matrix MATLAB code library freely accessible. The UV-visible absorption spectrum for experimental fitting was measured using a Beckman DU730 spectrophotometer. The finite element analysis software COMSOL Multiphysics with the RF module was used to model various geometries and conditions. The near- and far-field optical properties of AuNR can be solved numerically in the frequency domain using the scattered field formulation. The 3D simulation space was composed of three spherical volumes: nanorods, an embedding medium and a perfectly matched layer (PML). The embedding medium was air. A plane wave, used for excitation, was inserted on the inside of PMLs surrounding the embedding medium.

Figure 3:
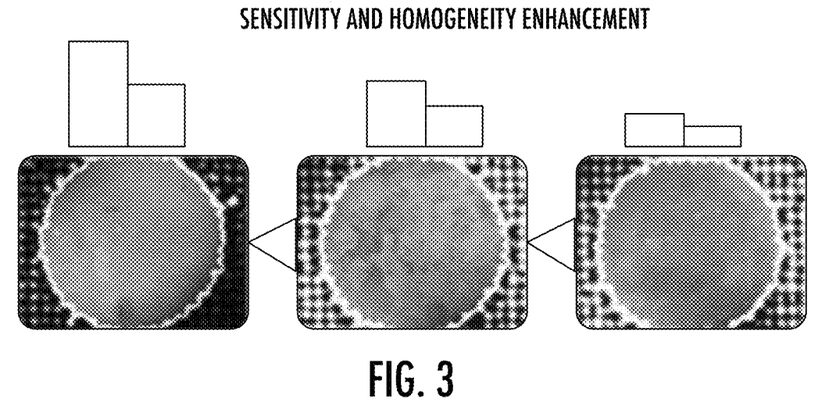
FIG. 3 is a schematic illustration of sensitivity and homogeneity enhanced dark-field assays acquired using the dark-field microscope system in accordance with the present disclosure.
Figure 4:
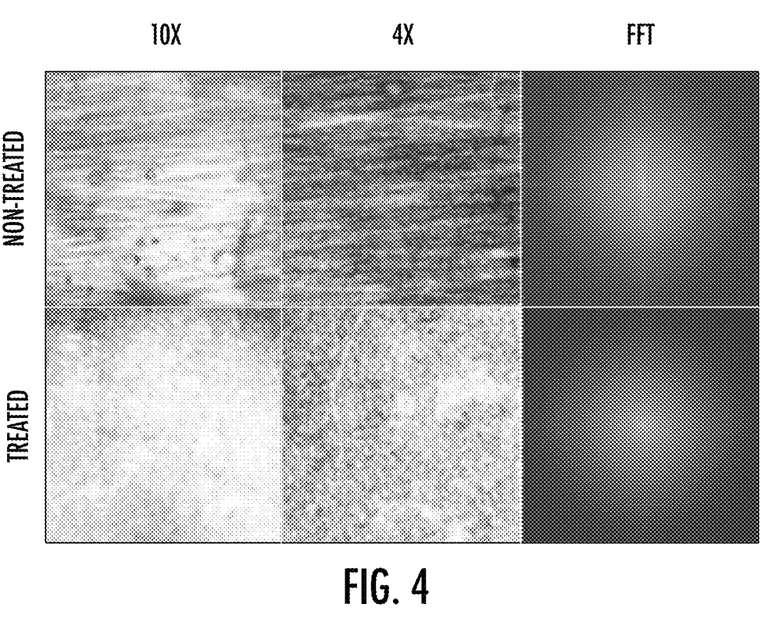
FIG. 4 are dark-field images acquired using the dark-field microscope system under 10× magnification, 4× magnification, and Fast Fourier Transform (FFT) images before and after pre-treatment steps.

Exemplary Results of Ultrasound and Heating Pre-Treatment Steps for LMDFA:

To analyze the effects of ultrasound and heating pre-treatment steps, nanoparticle dark-field images showing particle distribution were acquired using the dark-field microscope system 100 and compared under different magnifications between treated and non-treated slides, as shown in FIGS. 3-4. Images after ultrasound and heating treatment show enhanced homogeneity. Fast Fourier Transform (FFT) is a numerical technique to evaluate homogeneous properties of microstructures. FFT images map how much energy is at each spatial frequency. The center of the FFT images is the origin of frequency axes. White areas in the FFT images indicate the presence of energy. The clearer boundary of the white area after treatment reveals more randomness pattern at low frequency. The diagonal line shown only in non-treated FFT images suggested sharper gap between distributed and non-distributed areas of nanoparticles. The more converged FFT image after treatment validated that ultrasound and heat have the potential to solve the low homogeneity problem of LMDFA.

Figure 5A:
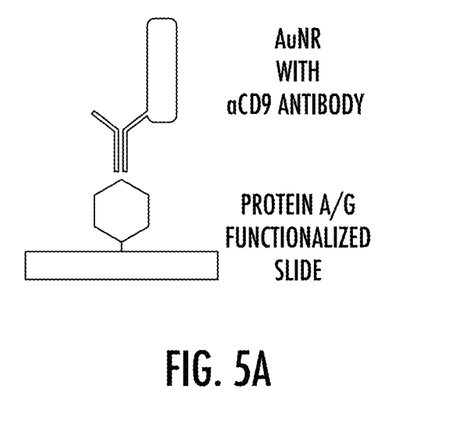
Figure 5B:
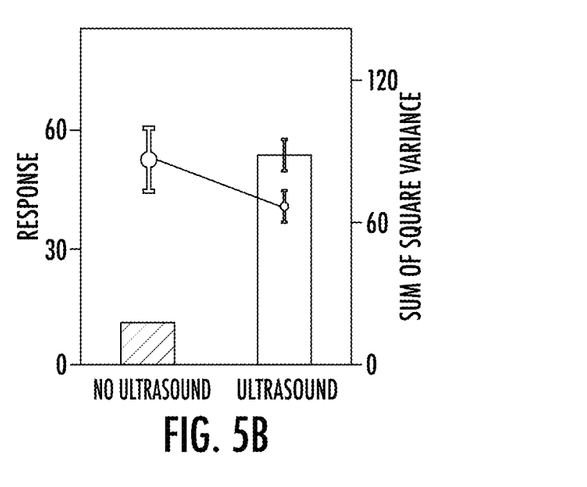
Figure 5C:
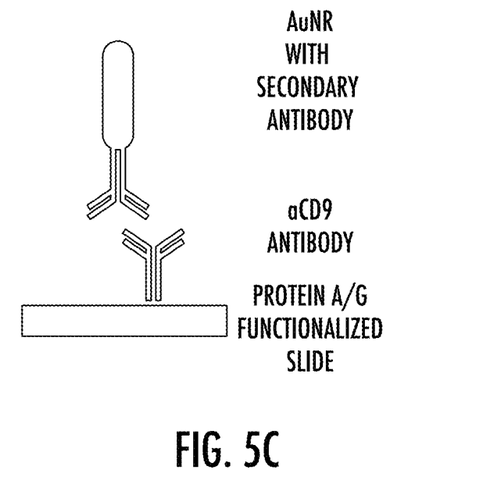
Figure 5D:
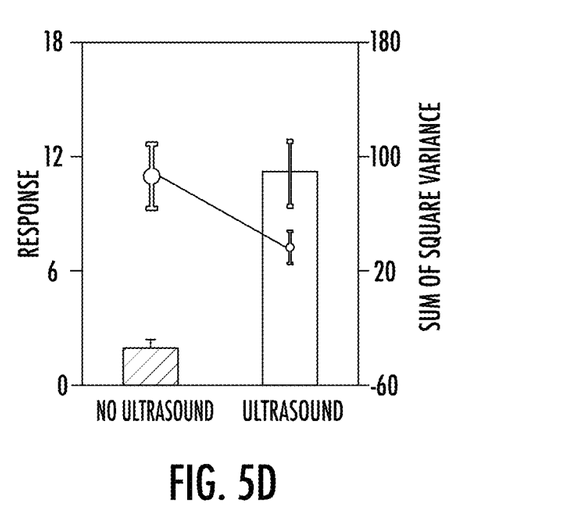
Figure 5E:
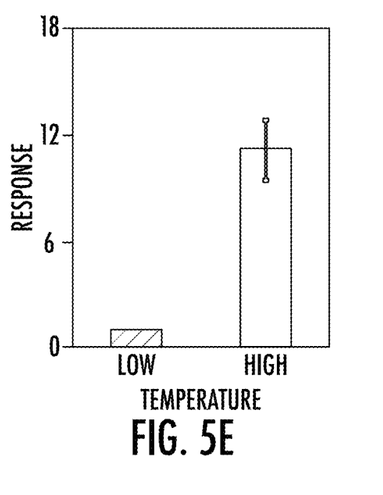

Direct binding and sandwich immunoassay were conducted to clarify the effect of ultrasound and heat separately using the pre-treatment device 104 described in FIG. 2. To quantify homogeneity, Sum of Square Variance (a), defined as $\Sigma_{i,j=0}^{N-1} P_{i,j} (i-j)^2$, where P is the pixel intensity in the image with i, j as locators, was employed as a reverse indicator. Lower σ indicates more homogenous distribution. Regardless assay type, both assays display higher response and lower a value after ultrasound treatment (FIGS. 5B and 5D), which become the numerical proof that the ultrasound can enhance both sensitivity and homogeneity for LMDFA. Heat also shown similar the effect to enhance the sensitivity by facilitating binding (FIG. 5E). As a by-product, treatment involving ultrasound and heat in LMDFA expedite the assay significantly. More than 14 times shorter assay duration could be achieved compared to non-treated LMDFA and conventional ELISA, as shown in Table 1.

TABLE 1

| Assay time consumption comparison | | | |
|---|---|---|---|
| | Assay Steps (hour) | | |
| | ELISA | Non-treated LMDFA | Treated LMDFA |
| Nanoparticle Conjugation | — | 3 | 0.25 |
| Surface Target Immobilization | 8 | 8 | 0.2 |
| Blocking | 1 | 1 | 0.5 |
| Sample loading | 8 | 8 | 0.2 |
| Primary Antibody | 2 | 2 | 0.2 |
| Secondary Antibody | 1 | — | 2* |
| Total | 20 | 22 | 1.35(3.35) |

*Optional for linker based amplification signal amplification

Figure 5F:
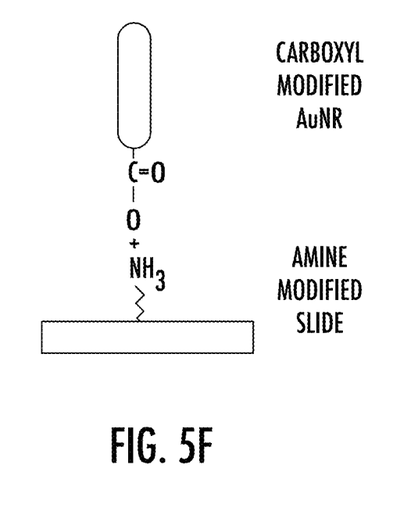
Figure 5G:
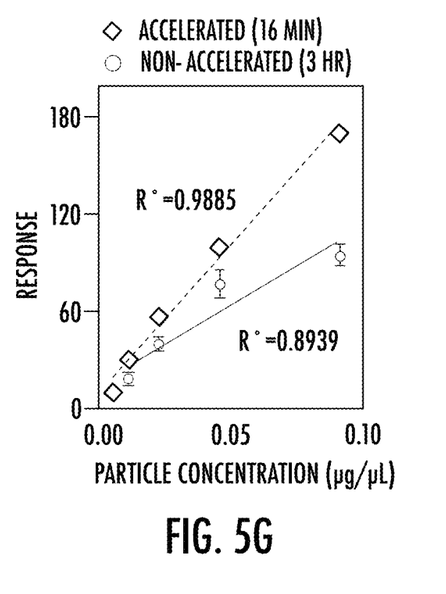
Figure 5H:
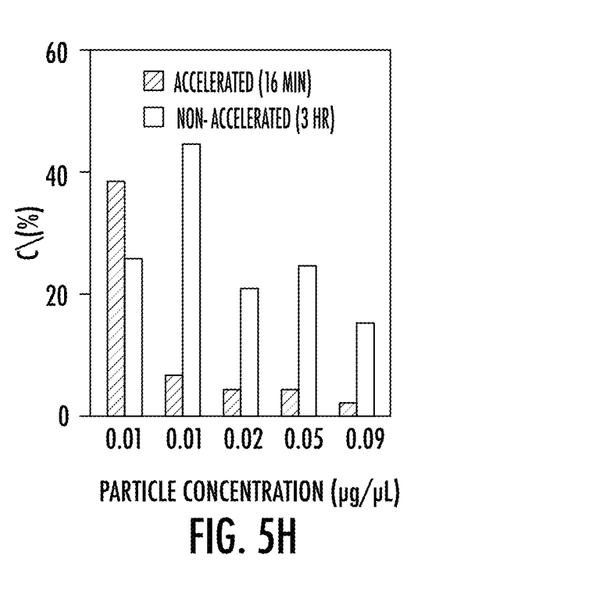

In addition, a direct binding assay quantifying nanoparticles were designed (FIG. 5F) aiming at evaluating linearity and coefficient of variance (CV) after treatment (FIGS. 5G and 5H). The superior linearity ($R^2=0.98$), repeatability (avg. 11%) and sensitivity (slope) with the accelerating treatment comparing to non-treated assay advocated a stable sensitive nanoparticle quantification assay using LMDFA.

Figure 6A:
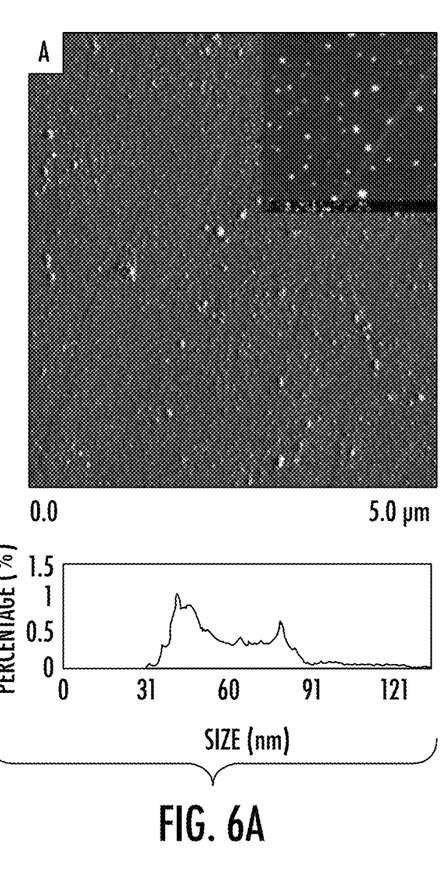
Figure 6B:
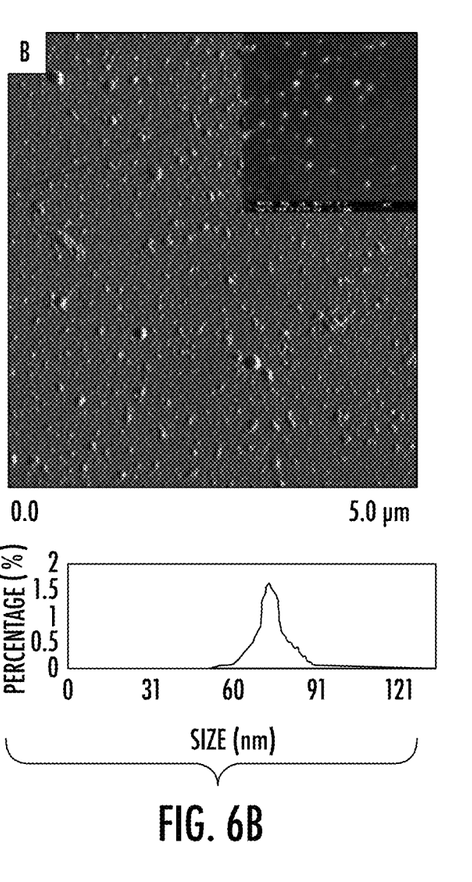

The dark-field microscope system 100 may be used to quantify exosomes in serum and cell culture medium. Ultrasonication is a well-accepted method for lysing the cell membrane. Since exosomes are covered by the same membrane as cells, the question arose when using the treatment for exosomes quantification. Ultrasound may jeopardize exosome quantification using LMDFA. To evaluate the exosome status before and after the treatment, AFM and SEM images were compared (FIGS. 6A and 6B). The counting result from SEM images shown 90% exosomes remains after treatment (62 vs. 69). Therefore, it is endurable to use the dark-field microscope system 100 for treatment and imaging of exosomes. Besides, the particle analysis from AFM images demonstrated the size filtering effect of the ultrasound on exosomes. Exosomes with smaller size were filtered after the treatment. It may benefit the exosomes based study because the larger membrane areas would potentially host more surface marker.

Theoretical Modeling and Simulation of Signal Amplification Scheme:

A signal amplification scheme based on proximity nanoparticles is also disclosed herein. To provide a theoretical rationale, numerical simulations were conducted. Finite-difference time-domain (FDTD), mie approximation (T-Matrix), and finite element method (FEM) are the most commonly used methods to compute the scattering of electromagnetic radiation by metallic nanoparticles. FDTD calculates field vector components in a given instant in time, and Fourier transfer near-field solution into the frequency domain and propagated into the far-field by surface or volume integration. FDTD simulation confirmed the scattering enhancement of proximity nanoparticles, but it is difficult to conduct large-scale simulation due to the computing complexity.

Figure 7A:
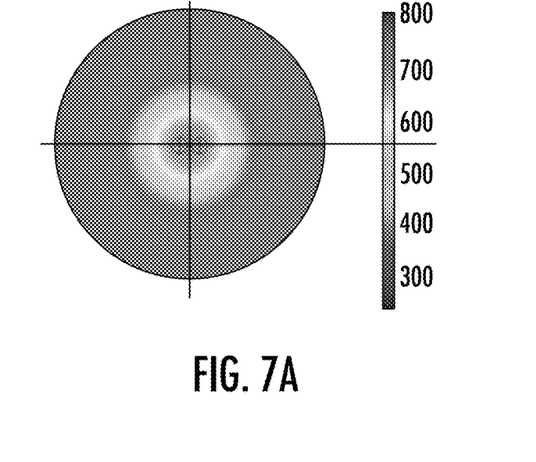
Figure 7B:
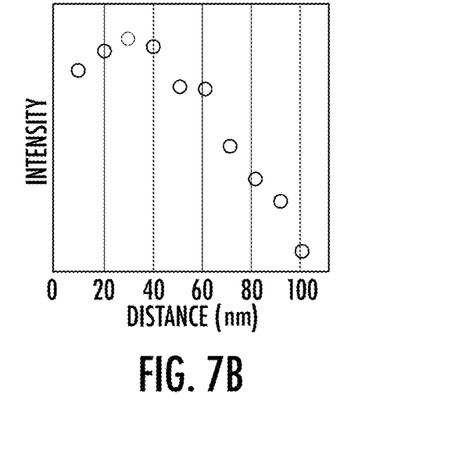
Figure 7C:
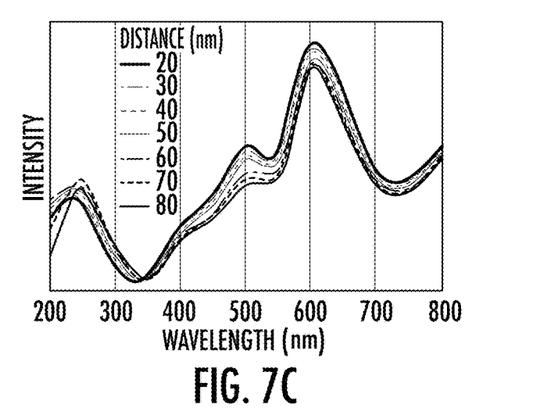
Figure 7D:
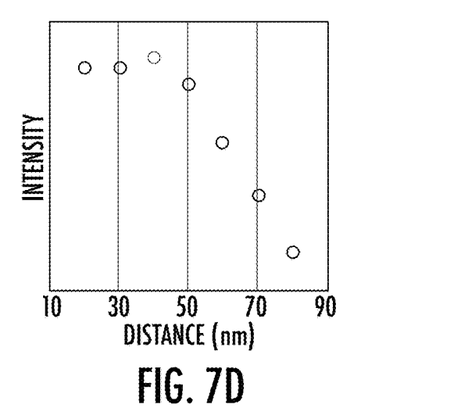

Mie approximation (T-Matrix) significantly simplified the Maxwell computing by considering the scattering of light from spherical objects. It is possible to approximate the scattering from ellipsoid objects, but is generally not suitable for nanorods with complex spatial configurations. The FEM method solves the scattering problem by discretizing Helmholtz equation which balances the computing complexity and is suitable for large-scale nanorods simulation. As shown in FIG. 7a, different distances between two proximity AuNR (Diameter and height: 25 nm, and 60 nm) were simulated under an incident light with a wavelength of 650 nm. The scattering intensity at the center of the two particles maximized when the distance reached 30 nm (FIG. 7b). Wavelength scanning versus different distances was also simulated (FIG. 7c). The integrated scattering intensity of all wavelength shown a maximum at 40 nm in distance. Those results suggested that for maximizing scattering signal, the amplification scheme should proximate the primary and secondary AuNR close or less than 30-40 nm.

Figure 7E:
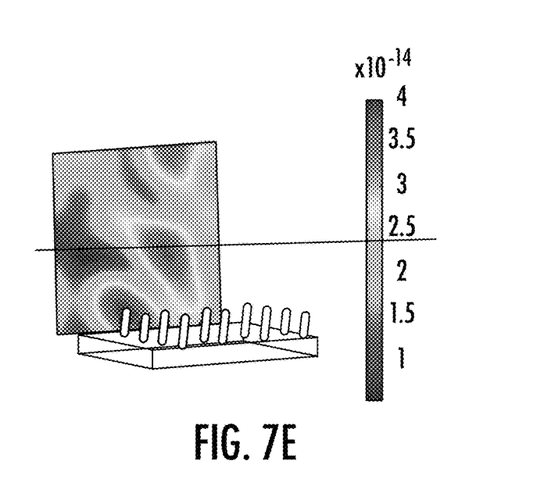
Figure 7F:
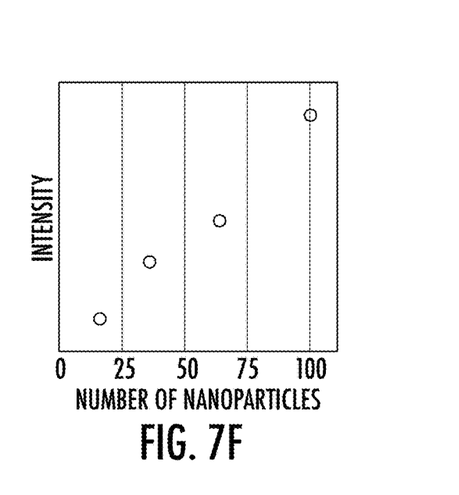

It becomes the rationale for using the PEG linker, as described above, with an MW of 1000 (the total distance ~20 nm). A scale-up simulation with a cluster of nanoparticles mimic the conditions of AuNR on the glass slide was designed as shown in (FIG. 7e). The incident light covered full spectrum emitted from the bottom side of the slide, and the detector was set perpendicular to the slide to collect the scattering light similarly set as under a darkfield microscope. The increasing scattering intensity along with ascending number of nanoparticles on the glass revealed the theoretical rationale for using LMDFA as a quantitative bioassay.

Figure 8A:
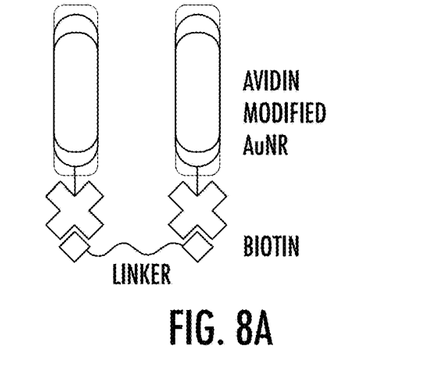
Figure 8B:
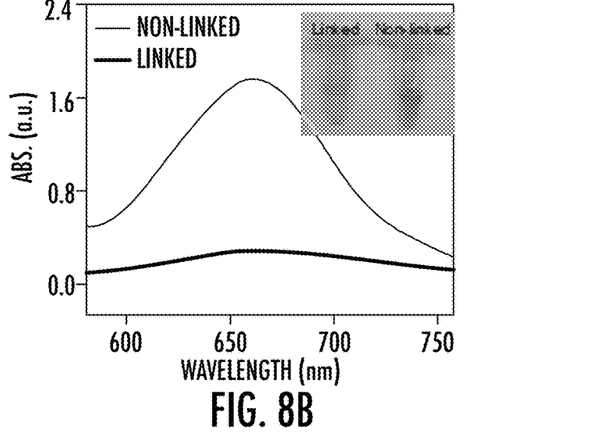
Figure 8C:
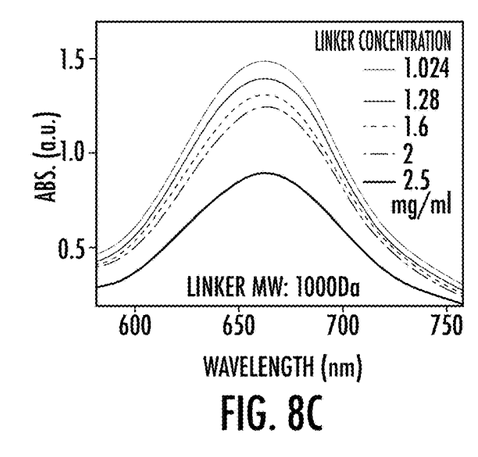
Figure 8D:
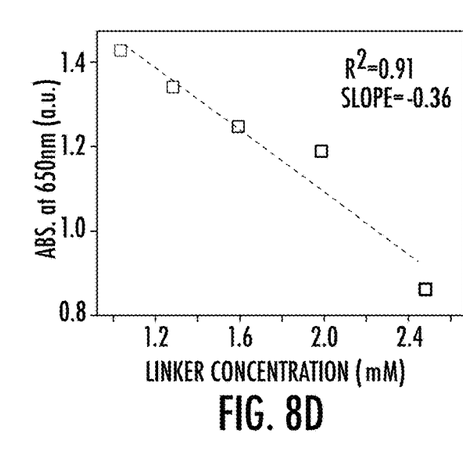
Figure 8E:
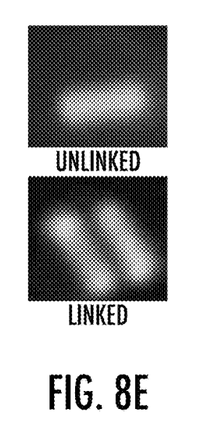
Figure 8F:
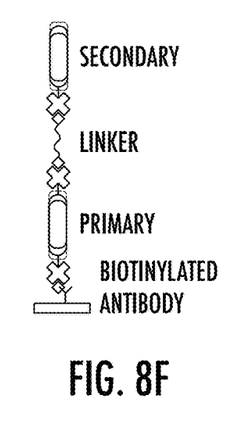
Figure 8G:
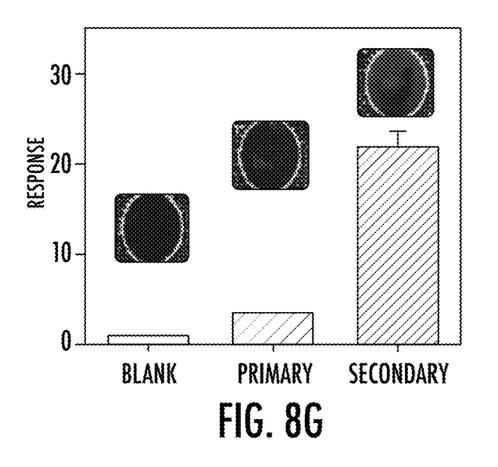

Signal Amplification:

Nanoparticles of noble metal are capable to enhance scattering by surface plasmon resonance. A pair of closely spaced metallic nanoparticle supports "dimer" plasmons that can enhance the scattering. In an attempt to amplify the signal for LMDFA, a linking strategy involving streptavidin modified AuNR and biotin-modified to form "dimer" was experimented first. Less absorption after dimer binding was observed, which implied more scattering. However, it has limited signal amplification and involves nanoparticle heterogeneously modified which increase translational difficulty. Hence, a homobifunctional biotinylated PEG derivative, bis-biotin functionalized polyethylene glycol (Biotin-PEG-Biotin) was introduced as a dimer linker (FIG. 8a). Adding the linker with a molecular weight (MW) of 1000 Da into streptavidin modified AuNR solution, the significant intensity decline of the absorption peak (FIG. 8b) suggested an effectively enhanced scattering. By controlling the linker concentration, the absorption peak intensity can be tunable, so as the scattering (FIGS. 8C and 8D). As an alternative, the same linker with MW of 400 Da was evaluated, but the linearity (0.94 vs 0.84) and absolute slope (0.36 vs 0.11) both lower than the 1000 Da ones. Applying the linker based scheme to LMDFA in a layer by layer pattern, 6.41 times signal amplification was obtained (FIGS. 8F and 8G). The result supports the LMDFA for more applications where higher sensitivity is necessary for quantification.

The present disclosure has described one or more preferred embodiments, and it should be appreciated that many equivalents, alternatives, variations, and modifications, aside from those expressly stated, are possible and within the scope of the invention.

We claim:

1. A method of using a low magnification dark-field microscope system for producing a dark-field image, the method comprising:
    transferring a biological specimen to a surface of a sample plate;
    heating the biological specimen on the sample plate using a heating device in an amount sufficient to enhance the binding affinity of the biological specimen to the sample plate;
    applying ultrasound energy to at least a portion of the biological specimen on the sample plate in an amount sufficient to enhance the binding affinity of the biological specimen to the sample plate, wherein the ultrasound energy is applied to the biological specimen using an ultrasound transducer that is communicatively coupled to an ultrasound generator; and
    imaging a region of interest the biological specimen on the sample plate using a dark-field microscope to generate a dark-field image of the biological specimen.

2. The method of claim 1, wherein the dark-field microscope system further comprises a processor, the processor having software stored therein and programmed to:
    process the dark-field image to determine an amount of the biological specimen within the region of interest.

3. The method of claim 1 wherein the sample plate includes a binding medium coupled to the surface of the plate, wherein the binding medium facilitates adhering the biological specimen to the surface of the sample plate.

4. The method of claim 1 wherein the dark field microscope system further comprises:
    a housing configured to receive a fluid medium; and
    a sample holder coupled to the housing and having a surface configured to receive the sample plate, the sample holder positioned to be at least partially submerged within the fluid medium.

5. The method of claim 4, wherein the dark field microscope system further comprises:
- a heat source configured to transfer heat to the fluid medium;
- a temperature sensor configured to monitor the temperature of the fluid medium in the housing;
- a controller communicatively coupled to the heat source and the temperature sensor, wherein the controller includes stored software therein and is programmed to:
  - receive temperature signals indicative of the temperature of the fluid medium; and
  - adjust the temperature of the fluid medium using the heat source to obtain a desired set-point temperature.

6. The method of claim 5, wherein the controller is programmed to regulate the desired set-point temperature between 25 degrees Celsius to 75 degrees Celsius.

7. The method of claim 5, wherein the heat source is coupled to at least a portion of an outer surface of the housing.

8. The method of claim 4, wherein the fluid medium comprises water.

9. The method of claim 1, wherein the dark field microscope system further comprises:
- a controller communicatively coupled to the ultrasound generator and the ultrasound transducer, wherein the controller includes stored software therein and is programmed to:
  - apply ultrasound energy to the biological specimen for a duration using the ultrasound transducer and the ultrasound generator.

10. The method of claim 9, wherein the controller is programmed to apply ultrasound energy to the biological specimen for at least 2 minutes.

11. The method of claim 9, wherein the controller is further programmed to:
- apply ultrasound energy intermittently to the biological specimen with a user-specified pause between each respective pulse of ultrasound energy.

12. The method of claim 4, wherein the ultrasound transducer is coupled to an outer surface of the housing.

13. The method of claim 1 wherein transferring a biological specimen to the surface of the sample plate further comprising doping the biological specimen with a metallic nanoparticle.

14. The method of claim 13, wherein the metallic nanoparticle comprises:
- a first protein modified with a first metallic nanorod;
- a second protein modified with a second metallic nanorod; and
- a linker that couples the first protein to the second protein.

15. The method of claim 14, wherein the first protein and the second protein comprise streptavidin.

16. The method of claim 14, wherein the first metallic rod and the second metallic rod comprise gold nanorods.

17. The method of claim 14, wherein the linker comprises bis-biotin coupled through functionalized polyethylene glycol.

18. The method of claim 13, wherein the metallic nanoparticle is coupled to an antibody.

19. The method of claim 1, wherein the surface has an immunoglobulin binding protein bound thereto.

20. The method of claim 1, wherein biological specimen comprises an exosome or an antibody.

* * * * *

UNITED STATES PATENT AND TRADEMARK OFFICE
CERTIFICATE OF CORRECTION

PATENT NO. : 11,402,620 B2
APPLICATION NO. : 17/420102
DATED : August 2, 2022
INVENTOR(S) : Ye Hu et al.

It is certified that error appears in the above-identified patent and that said Letters Patent is hereby corrected as shown below:

In the Specification

Column 8, Line 29, "Variance (a), defined" should be --Variance ($\sigma$), defined--.

Column 8, Line 34, "lower a value" should be --lower $\sigma$ value--.

Signed and Sealed this
Fourth Day of October, 2022

Katherine Kelly Vidal
*Director of the United States Patent and Trademark Office*